United States Patent
Kawatahara (10) Patent No.: US 7,179,230 B2
(45) Date of Patent: Feb. 20, 2007

(54) PULSIMETER AND MEASURING SYSTEM COMPRISING THE SAME

(75) Inventor: Masanao Kawatahara, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 10/258,458

(22) PCT Filed: Apr. 24, 2001

(86) PCT No.: PCT/JP01/03542

§ 371 (c)(1),
(2), (4) Date: Oct. 23, 2002

(87) PCT Pub. No.: WO01/80733

PCT Pub. Date: Nov. 1, 2001

(65) Prior Publication Data

US 2003/0142588 A1    Jul. 31, 2003

(30) Foreign Application Priority Data

Apr. 25, 2000 (JP) .............................. 2000-124766

(51) Int. Cl.
*A61B 5/02* (2006.01)

(52) U.S. Cl. .................. 600/502; 600/300; 600/500

(58) Field of Classification Search ........ 600/300–301, 600/310–344, 481, 500–507, 509, 364, 365, 600/473, 476, 200; 180/287; 235/462, 472
See application file for complete search history.

(56) References Cited

U.S. PATENT DOCUMENTS

| | | | | |
|---|---|---|---|---|
| 3,908,636 A | * | 9/1975 | Page ........................ 600/479 |
| 4,121,574 A | * | 10/1978 | Lester ...................... 600/479 |
| 4,791,933 A | | 12/1988 | Asai et al. |
| 5,184,005 A | * | 2/1993 | Ukai et al. ............. 235/462.16 |
| 5,193,855 A | * | 3/1993 | Shamos ..................... 283/117 |
| 5,228,449 A | * | 7/1993 | Christ et al. ................ 600/504 |
| 5,351,695 A | * | 10/1994 | Mills et al. ................. 600/508 |
| 5,650,982 A | * | 7/1997 | Takenaka et al. ............. 368/10 |
| 5,676,139 A | * | 10/1997 | Goldberger et al. ......... 600/310 |
| 5,687,717 A | * | 11/1997 | Halpern et al. ............. 600/300 |
| 5,697,376 A | * | 12/1997 | Nomura et al. ............. 600/300 |
| 5,729,203 A | * | 3/1998 | Oka et al. ................ 340/573.1 |
| 5,766,132 A | * | 6/1998 | Yasukawa et al. ........... 600/503 |
| 5,810,736 A | * | 9/1998 | Pail ........................ 600/500 |
| 5,845,733 A | * | 12/1998 | Wolfsen .................... 340/5.53 |
| 5,916,229 A | * | 6/1999 | Evans ....................... 606/171 |
| 5,919,141 A | * | 7/1999 | Money et al. .............. 600/513 |
| 5,997,476 A | * | 12/1999 | Brown ...................... 600/300 |

(Continued)

FOREIGN PATENT DOCUMENTS

EP    0666055    8/1995

(Continued)

*Primary Examiner*—Charles A Marmor, II
*Assistant Examiner*—Patricia C Mallari
(74) *Attorney, Agent, or Firm*—Hamre, Schumann, Mueller & Larson, P.C.

(57) ABSTRACT

A measuring system includes a measuring apparatus (2) for obtaining pulse data and identification data related to the pulse data, and a central controlling apparatus (1, 3) for receiving the pulse data and the identification data from the measuring apparatus. The central controlling apparatus includes a data processing unit (1) for performing data processing based on the pulse data and the identification data.

6 Claims, 5 Drawing Sheets

U.S. PATENT DOCUMENTS

| | | | | |
|---|---|---|---|---|
| 5,997,483 A | * | 12/1999 | Johnson | 600/538 |
| 6,537,225 B1 | * | 3/2003 | Mills | 600/481 |
| 6,618,602 B2 | * | 9/2003 | Levin | 600/323 |
| 6,671,563 B1 | * | 12/2003 | Engelson et al. | 700/2 |

FOREIGN PATENT DOCUMENTS

| | | |
|---|---|---|
| EP | 0 922 434 | 6/1999 |
| FR | 2 655 834 | 6/1991 |
| JP | 04-34809 | 8/1992 |
| JP | 09-131326 | 5/1997 |
| JP | 11-099130 | 4/1999 |
| JP | 11-146867 | 6/1999 |

* cited by examiner

| ID | Name | Pulse Rate | Lactic Acid Level |
|---|---|---|---|
|  |  |  |  |
|  |  |  |  |
|  |  |  |  |

PULSIMETER AND MEASURING SYSTEM COMPRISING THE SAME

TECHNICAL FIELD

The present invention relates to a pulsometer and a measuring system using the same.

BACKGROUND ART

Conventionally, swimming is adopted in fitness facilities or the like as one of the programs for enhancing physical strength. Swimming is utilized also for medical treatment. In water, a large load is not exerted on a patient's knee joints and the like, because part of his or her weight is borne by buoyancy. Therefore, swimming is suitable for kinesitherapy for diabetics or the like who suffer from arthralgia.

In such kinesitherapy, it is generally difficult to judge, from the facial expression or the body motion of the patient, whether the exercise being performed by the patient is exerting a proper load on the patient. Therefore, the degree of a load by the exercise is often checked by measuring the pulse rate of the patient, for example.

Conventionally, various pulse measuring apparatuses are developed. However, such apparatuses are not satisfactorily waterproof for use at a poolside, or even when satisfactorily waterproof, they are not suitable for use in water. For example, usually, the use of a pulsimeter having a watch function in water is not allowed.

DISCLOSURE OF THE INVENTION

The present invention is conceived under the circumstances described above. It is, therefore, an object of the present invention is to provide a novel pulsimeter which is sufficiently waterproof and which can be used at a pool. Another object of the present invention is to provide a measuring system utilizing such a novel pulsimeter.

According to a first aspect of the present invention, there is provided a pulsimeter comprising a waterproof housing, a first panel attached to the housing, a pulse sensor arranged in the housing in facing relationship to the first panel for detecting pulse data, a display for displaying a pulse count per unit time based on the pulse data, a communication unit for performing data communication with an external device, and a controller for transmitting the pulse data to the external device via the communication unit.

According to a preferred embodiment of the present invention, the pulse sensor includes a light emitting element for irradiating a detection object, and a light receiving element for detecting a light reflected by the detection object.

Preferably, the data communication is performed wirelessly.

Preferably, additionally to the pulse data, the pulse sensor detects identification data related to the pulse data.

According to another preferred embodiment of the present invention, the pulsimeter further comprises an identification data inputting unit provided separately from the pulse sensor for inputting identification data related to the pulse data.

Preferably, the pulsimeter further comprises a second panel supported by the housing, and the identification data inputting unit is arranged in the housing in facing relationship to the second panel.

Preferably, the housing is configured like a dome having a top. The first panel is arranged adjacent the top, and the second panel is farther from the top than the first panel is.

Preferably, the pulse sensor also serves as the communication unit.

Preferably, the pulsimeter further comprises a rechargeable power source provided in the housing. The power source is charged by an external recharging device in a non-contact manner.

According to a second aspect of the present invention, there is provided a measuring system comprising a measuring apparatus for obtaining pulse data and identification data related to the pulse data, and a central controlling apparatus for receiving the pulse data and the identification data from the measuring apparatus. The central controlling apparatus includes a data processing unit for performing data processing based on the pulse data and the identification data.

BEST MODE FOR CARRYING OUT THE INVENTION

The present invention will be described below in detail with reference to the accompanying drawings.

Figure 1:
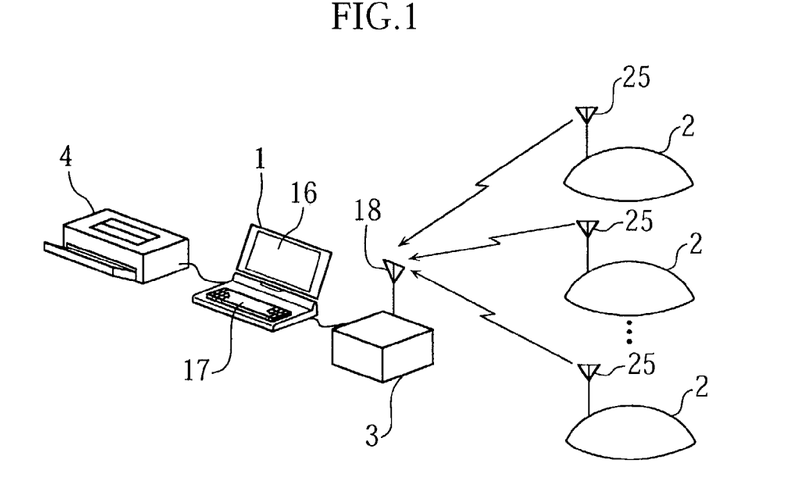
FIG. 1 schematically illustrates a measuring system utilizing a pulsimeter according to a first embodiment of the present invention.

FIG. 1 illustrates a pulsimeter according to a first embodiment of the present invention, and a measuring system using the pulsimeter. The illustrated measuring system includes a host computer 1 (hereinafter, simply referred to as "host"), and a plurality of pulsimeters 2 for performing data communication with the host 1. In the illustrated example, a communication apparatus 3 is provided for wirelessly connecting the host 1 to each of the pulsimeters 2. The host 1 is connected to a printer 4 for printing the results of the data processing.

The measuring system of FIG. 1 may be utilized for measuring a pulse of trainees of a swim school for example. In this case, the host 1, the communication apparatus 2 and the printer 4 may be arranged in a trainers' room near a pool, for example, for operation by a trainer of the swim school. The pulsimeters 2 may be disposed at a poolside for easy access by the trainees.

Though the host 1 illustrated in FIG. 1 is a notebook PC which is convenient for carriage, the present invention is not limited thereto. For example, the host 1 may be of a desktop type incorporating a wireless communication unit.

Figure 2:
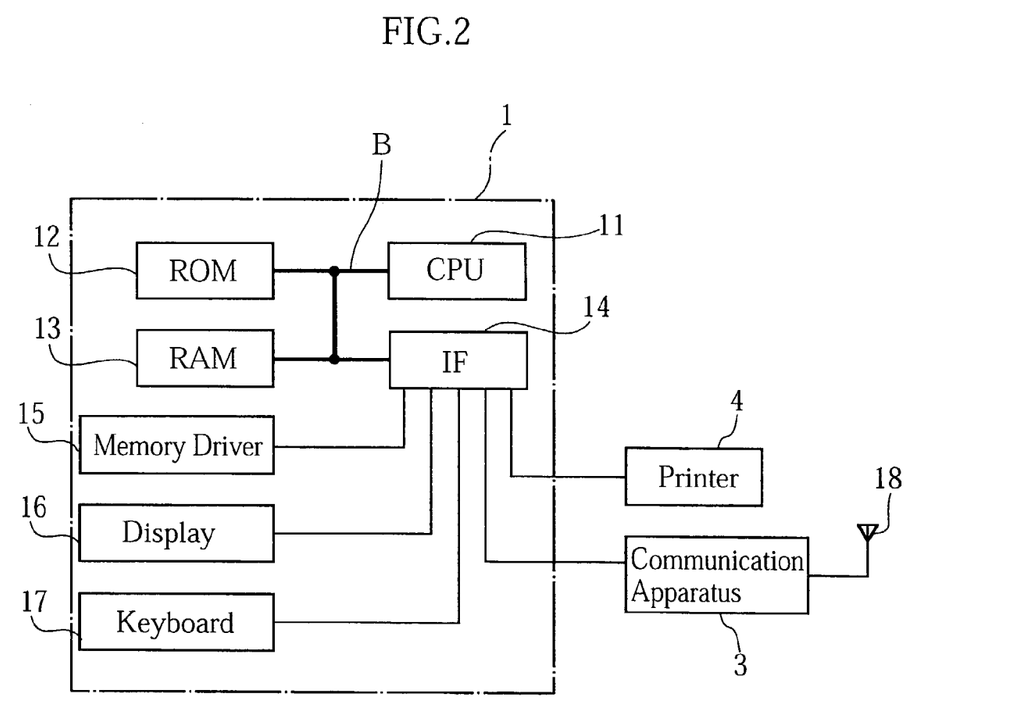
FIG. 2 is a block diagram of principal structural parts of a host computer used in the system shown in FIG. 1.

As shown in FIG. 2, the host 1 includes a CPU (central processing unit) 11, a ROM (read only memory) 12, a RAM (random access memory) 13, an IF (interface) 14, a memory driver 15, a display 16 and a keyboard 17. The memory driver 15 drives and controls the built-in hard disk memory and an external storage medium (such as a flexible disk or a CD-ROM). The CPU 11, the ROM 12, the RAM 13 and the IF (interface) 14 are connected to each other via bus lines B. The memory driver 15, the display 16 and the keyboard 17 are connected to the IF 14. Since each of the components 11–17 is conventionally known, the description of the function and operation principle of the component will be omitted.

The communication apparatus 3 and the printer 4 are connected to the IF 14 of the host 1. The communication apparatus 3 receives wireless signals transmitted from each The communication apparatus 3 and the printer 4 are connected to the IF 14 of the host 1. The communication apparatus 3 receives wireless signals transmitted from each of the pulsimeters 2. Specifically, the communication apparatus 3 is provided with a receiving antenna 18 for receiving pulse data and the like transmitted from each pulsimeter 2. The received data is transmitted to the CPU 11 of the host 1.

The printer 4 prints the pulse count of each trainee per unit time (1 minute for example) on a recording paper based on the print data and the print instruction data transmitted from the CPU 11. According to the present invention, in addition to the pulse rate, the lactic acid level in muscle of the trainee may be printed on the recording paper. It is generally known that there is a correlation between the lactic acid level in muscle and the pulse rate. Therefore, the lactic acid level in muscle of a trainee can be inferred from the measurement of the pulse rate of the trainee if the correspondence between the pulse rate and the lactic acid level in muscle of the trainee is determined in advance. The pulse rate and the lactic acid level of each trainee thus obtained may be printed on the recording paper as a table or a graph.

Figure 3:
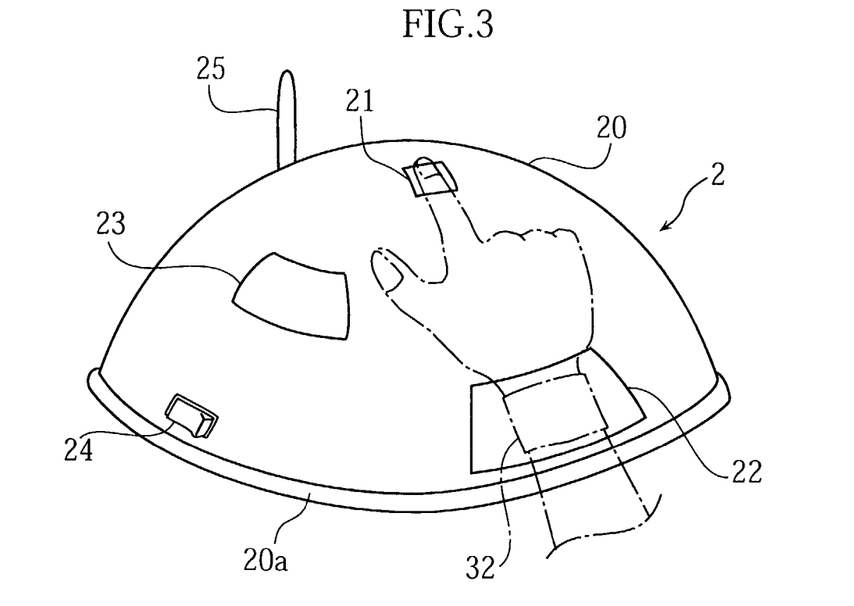
FIG. 3 is a schematic view illustrating a pulsimeter used in the system of FIG. 1.

As shown in FIG. 3, the pulsimeter 2 according to the present invention includes a dome-shaped hollow housing 20 formed of a resin material for example. The housing 20 is provided with a first panel 21 arranged adjacent the top of the housing, a second panel 22 spaced downward from the first panel 21, a display 23 for displaying a pulse rate and a power switch 24. Each of the first panel 21 and the second panel 22 maybe formed of a transparent glass material for example. The display 23 may be a liquid crystal display. Alternatively, however, use may be made of a 7-segment LED display, a plasma display or the like.

Each of the first panel 21, the second panel 22 and the display 23 is closely fitted in an opening formed in the housing 20. Although the housing 20 is open downwardly (in FIG. 3), the opening is tightly sealed with a circular base 20a. This structure prevents water from entering the pulsimeter 2.

In using the pulsimeter 2, a trainee (user) winds a wristband 32 provided with an ID tag 33 (See FIG. 4) around his or her right wrist for example, as indicated by phantom lines in FIG. 3. The ID tag 33 stores the identification information peculiar to the trainee. When the trainee puts his or her right forefinger on the first panel 21, the wristband 32 (and the ID tag 33) comes into facing relationship to the second panel 22. Though not illustrated, a guide member may be provided at and/or adjacent the first panel for bringing the fingertip into reliable contact with the panel 1.

Figure 4:
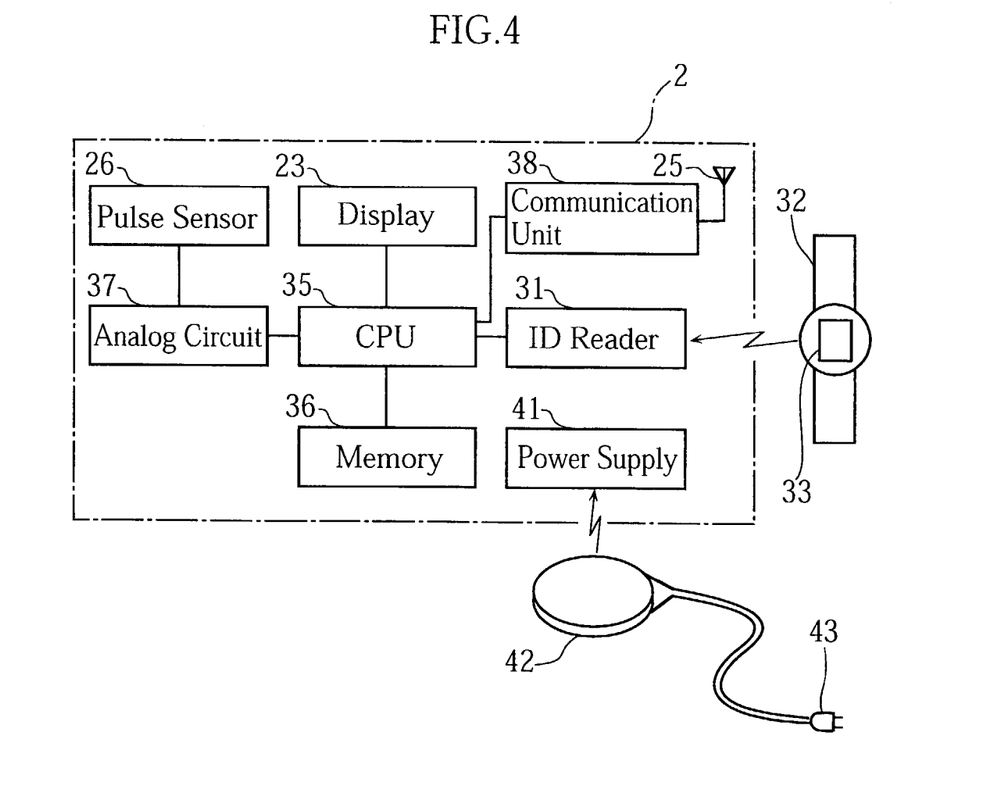
FIG. 4 is a block diagram illustrating principal structural parts of the pulsimeter of FIG. 3.
Figure 5:
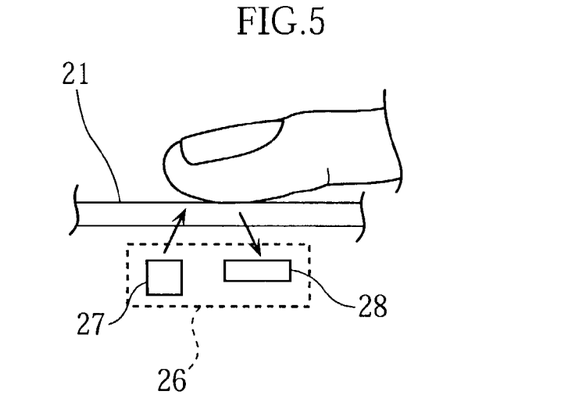
FIG. 5 is a schematic view illustrating the function of a pulse sensor used in the pulsimeter of FIG. 3.

The pulsimeter 2 includes a pulse sensor 26 (FIG. 4). As shown in FIG. 5, the pulse sensor 26 is arranged in facing relationship to the inner surface of the first panel 21. The pulse sensor 26 includes a light emitting element 27 and a light receiving element 28. The light emitting element 27 may be a light emitting diode for example, whereas the light receiving element 28 may be a phototransistor for example.

The operation principle of the pulse sensor 26 is as follows. With a finger of the trainee put on the first panel 21, the capillaries at the fingertip are irradiated with a light emitted from the light emitting element 27. The irradiating light is partially reflected by the blood flowing through the capillaries and the reflected light is detected by the light receiving element 28. Since the concentration of blood flowing through the capillaries varies depending on the pulsation of the blood, the proportion of light reflected also varies depending on the pulsation. Therefore, the pulse count of the trainee per unit time can be determined by analyzing the reflected light detected by the light receiving element 28.

For reading the ID information of the trainee from the ID tag 33, an ID reader 31 (FIG. 4) is provided in facing relationship to the inner surface of the second panel 22. The ID tag 33 includes an IC chip (not shown) provided with a memory and a CPU, and a coil antenna (not shown). The IC chip is driven by the electromagnetic wave energy supplied from the ID reader 31. The trainee's identification data, which is stored in the memory of the ID tag 33 in advance, is transmitted to the ID reader 31 through the coil antenna. The memory of the ID tag 33 may be capable of storing 64-bit data for example. Alternatively, the ID reader 31 may read the trainee's identification data stored in the ID tag 33 by conventional optical or magnetic data reading means.

As shown in FIG. 4, additionally to the display 23, the pulse sensor 26 and the ID reader 31, the pulsimeter 2 includes a CPU 35, a memory 36, an analog circuit 37, a communication unit 38 and a power supply 41. The CPU 35 controls the entire operation of the pulsimeter 2 in accordance with an execution program stored in the memory 36. The memory 36 comprises, for example, a ROM for storing the execution program, and a RAM for storing various data and for providing the CPU 35 with a work area.

The pulse information detected by the pulse sensor 26 is converted into electric signals for transmission to the analog circuit 37. The analog circuit 37 converts the received electric signals into digital signals while amplifying the signals. The analog circuit 37 also performs sample-and-hold processing and the like with respect to the received electric signals. The electric signals (digital signals) thus processed are transmitted to the CPU 35.

The communication unit 38 for performing wireless communication with the host 1 is provided with a transmitter (not shown). The communication unit 38 is connected to a transmitting antenna 25. Such wireless communication between the host 1 and each pulsimeter 2 is advantageous, because, unlike the wire communication, the wetting of a connection cable does not occur.

As described above, the ID reader 31 reads data from the ID tag 33 of the wristband 32. The read identification data is transmitted to the CPU 35.

The power supply 41A includes a rechargeable battery such as a lithium ion battery. As shown in FIG. 4, the rechargeable battery is recharged by an external recharging head 42 in a non-contact manner. Specifically, the recharging head 42 is driven by commercial power supplied through a connector 43. The recharging head 42 incorporates an electric power supplying coil (not shown), whereas the power supply 41 incorporates an electric power receiving coil (not shown). When the recharging head 42 is driven, the rechargeable battery of the power supply 41 is charged due to the electromagnetic induction generated between the power supplying coil and the power receiving coil. In this way, electric power can be supplied from the recharging head 42 to the power supply 41 in a con-contact manner. Therefore, the housing 2 and the base 20*a* (FIG. 3) need not be formed with a through-hole for inserting a power supply cable, so that the water-proofing property of the pulsimeter 2 is not deteriorated.

Figure 6:
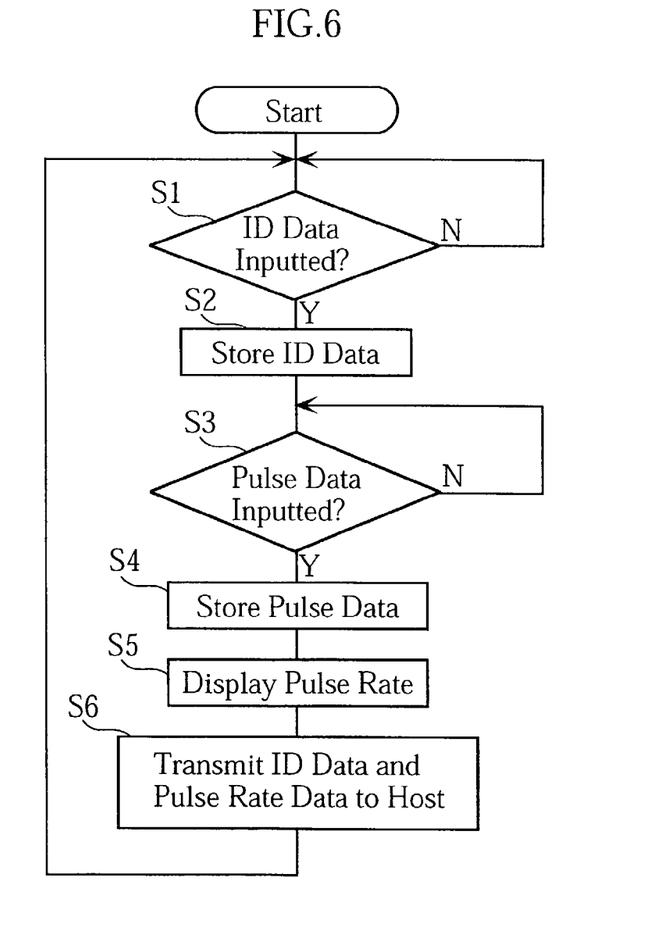
FIG. 6 is a flowchart illustrating the operation of the pulsimeter of FIG. 3.

Next, the operation at the CPU 35 of the pulsimeter 2 will be described with reference to the flowchart shown in FIG. 6. First, when the power switch 24 (See FIG. 3) of the pulsimeter 2 is turned on, the CPU 35 checks whether or not the identification data is read by the ID reader 31. In this stage, when a trainee places his or her right hand at the pulsimeter as shown in FIG. 3, the identification data stored in the ID tag 33 is read by the ID reader 31 and transmitted to the CPU 35. Thus, the CPU 35 determines that the identification data is inputted (S1: YES). More specifically, the CPU 35 determines that the transmitted data is the identification data in the case where the data is formed in accordance with a predetermined identification data format.

When the CPU 35 determines that the identification data is inputted in S1, a short beep may be outputted only once from a non-illustrated speaker of the pulsimeter 2. This notifies the trainee that the identification data is read by the pulsimeter 2.

When the identification data is not inputted (S1: NO), the CPU continues to monitor the inputting of the identification data.

If "YES" in S1, the inputted identification data is stored in the memory 36 of the pulsimeter 2 (S2).

Then, the CPU 35 checks whether or not the pulse data is inputted (S3). Specifically, when the pulse data detected by the pulse sensor 26 is transmitted to the CPU via the analog circuit 37, the CPU determines that the pulse data is inputted (S3: YES). In other cases, the CPU determines that the pulse data is not inputted (S3: NO). Preferably, when the pulse data is inputted, a short beep may be outputted twice from the non-illustrated speaker. This notifies the trainee that the pulse data is read properly.

In the above-described case, the CPU 35 checks whether the pulse data is inputted after confirming the inputting of the identification data of the trainee. However, the present invention is not limited thereto. Alternatively, whether the identification data is inputted may be checked after confirming the inputting of the pulse data.

If "YES" in S3, the pulse count of the trainee per unit time is computed based on the pulse data, and the result is stored in the memory 36 (S4).

Subsequently, the CPU 35 displays the calculated pulse rate at the display 23 (S5). This enables the trainee to immediately realize his or her pulse rate.

Then, the CPU 35 transmits the identification data and the pulse data to the host 1 (S6). Specifically, the CPU 35 reads the identification data and the pulse data from the memory 36 and transmits these data to the communication unit 38. The communication unit 38 modulates these data and transmits them via the transmitting antenna 25 together with the carrier.

These signals are received by the receiving antenna 18 of the communication unit 3 and then transmitted to the host 1. The frequency of the carrier, the data format, and the transmission protocol are decided in advance between the communication apparatus 3 and the communication unit 3, so that the communication apparatus 3 can properly receive the identification data and the pulse data. A check code may be added to the pulse data or the identification data to detect a transmission error.

Figure 7:
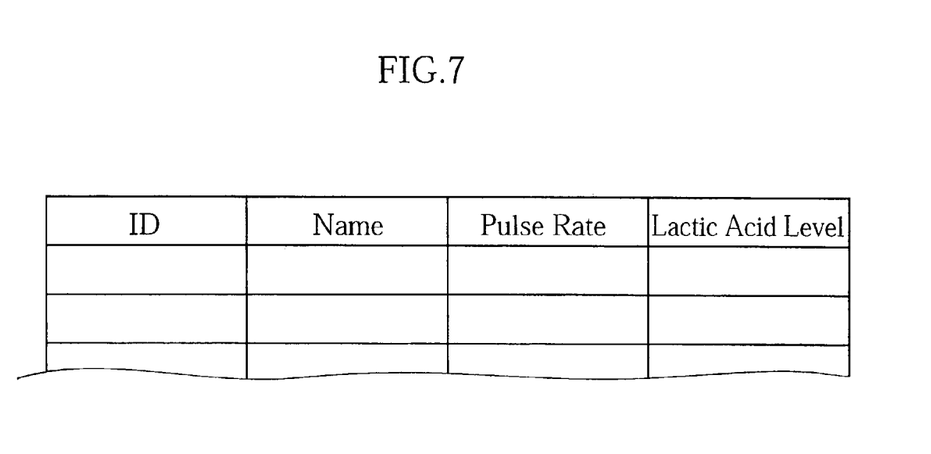
FIG. 7 illustrates an example of format for displaying data detected by the pulsimeter of FIG. 3.

Upon receiving the data, the host 1 determines, based on the identification data, which trainee's pulse data the received pulse data is. Further, the host 1 computes the lactic acid level of the trainee from the pulse data. The pulse rate and the estimated lactic acid level of each trainee may be displayed at the display 16 as a table as shown in FIG. 7 for example. Instead of the table (or in addition to the table), the data obtained by the pulsimeter 2 may be displayed as a graph. The table of FIG. 7 may be printed by the printer 4 as required. When the obtained pulse rate or the lactic acid level is abnormal, that particular value may be blinked on the display 16 to attract a trainer's attention. Alternatively, a vocal warning may be outputted from the speaker of the host 1.

The above-described embodiment is advantageous in that the pulse and the identification data of a trainee can be obtained at the same time. The housing 20 need not necessarily be dome-shaped as illustrated, but may otherwise be configured.

Figure 8:
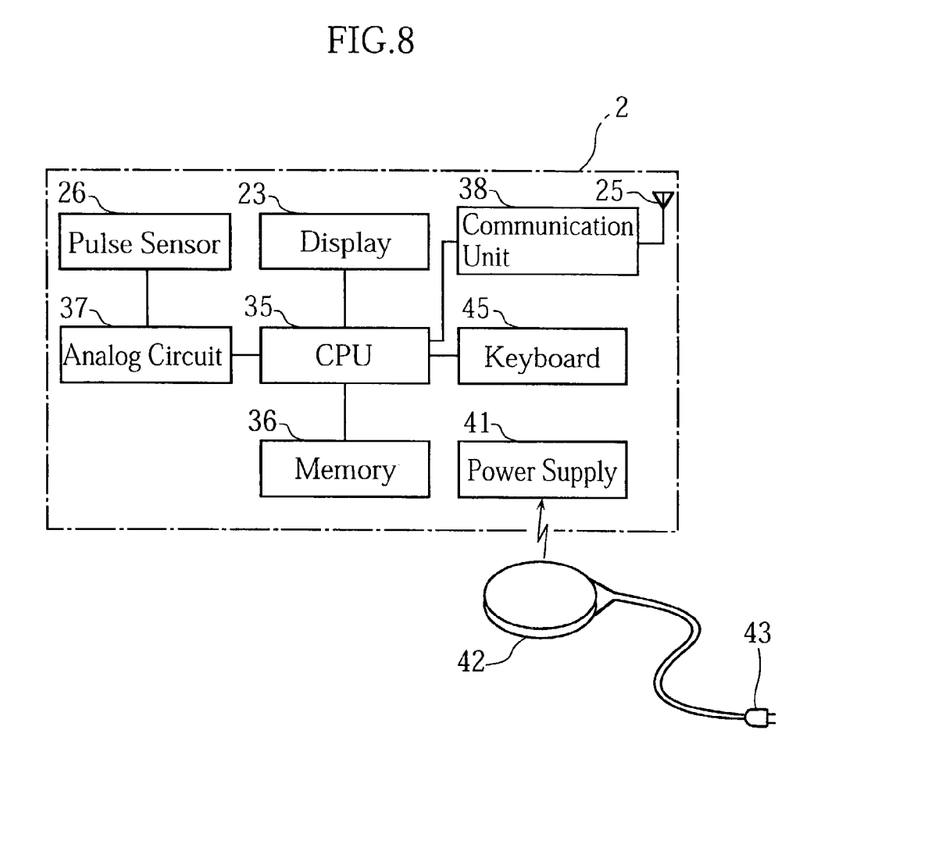
FIG. 8 is a block diagram illustrating principal structural parts of a pulsimeter according to a second embodiment of the present invention.

FIG. 8 illustrates principal structural elements of a pulsimeter according to a second embodiment of the present invention. As will be understood from the comparison of FIG. 8 with FIG. 4 (the first embodiment), the pulsimeter 2 of the second embodiment is basically the same in structure as the pulsimeter of the first embodiment, but differs in that a keyboard 45 is used instead of the ID reader 31. The keyboard 45 is connected to the CPU 35 so that the trainee inputs his or her identification data via the keyboard 45.

Figure 9:
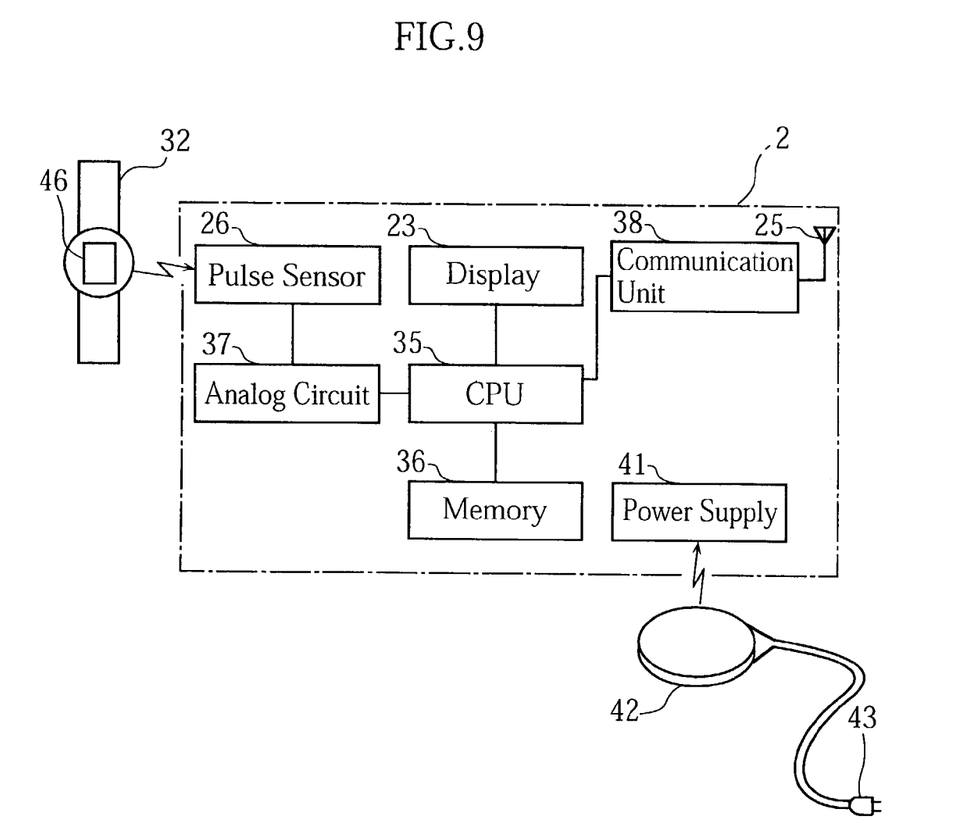
FIG. 9 is a block diagram illustrating principal structural parts of a pulsimeter according to a third embodiment of the present invention.

FIG. 9 illustrates principal structural elements of a pulsimeter according to a third embodiment of the present invention. Similarly to the second embodiment, the pulsimeter 2 of the third embodiment is basically the same in structure as the pulsimeter of the first embodiment, but differs in that the pulse sensor 26 detects the identification information of a trainee in addition to the pulse rate. Therefore, the pulsimeter 2 of the third embodiment requires neither the ID reader 31 (the first embodiment) nor the keyboard 45 (the second embodiment).

The pulse sensor 26 detects the identification information as follows. As shown in FIG. 9, a trainee puts on a wristband 32 provided with an infrared emitter 46. Though not illustrated, the infrared emitter 46 includes a CPU, a memory, a transmission unit, a light emitting diode and an output switch. The identification information of the trainee is stored in the memory in advance. When the output switch is pushed by the trainee, the CPU reads the identification information recorded in the memory and instructs the transmission unit to transmit the identification information. Based on the instruction, the transmission unit drives the light emitting diode to output infrared ray in accordance with the identification information of the trainee. The infrared ray is detected by the pulse sensor 26. The detected signal is transmitted to a CPU 35 through an analog circuit 37 for analysis. As a result, the identification information of the trainee is recognized.

Although the data transmission between the pulsimeter 2 and the host 1 is performed wirelessly in each of the above-described embodiments, the present invention is not limited thereto. Instead of the wireless communication, a removable portable data storage unit may be used for the pulsimeter 2. Specifically, in obtaining the pulse rate and the identification information of a trainee, the data storage unit is directly connected to the pulsimeter. For example, the data storage unit may be inserted in a socket provided in the pulsimeter for electrical connection thereto. The pulse data and the identification information detected by the pulsimeter are stored in an appropriate memory provided in the data storage unit. Thereafter, the data storage unit is removed from the pulsimeter and brought to the host 1. Finally, the data storage unit is connected to the host 1 via a cable or the like for outputting the stored data to the host 1.

Figure 10:
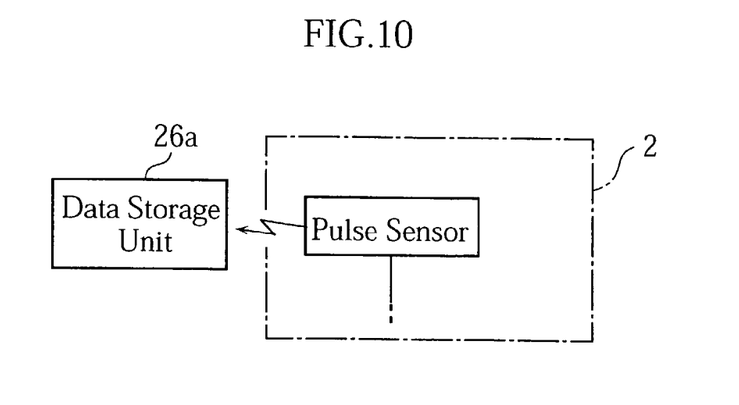
FIG. 10 is a schematic view illustrating a modification of the pulsimeter according to the third embodiment of the present invention.

Instead of using the socket, the data communication between the data storage unit 26a and the pulse sensor 26 may be performed by the IrDA method, as shown in FIG. 10. In this case, the provision of the communication unit 38 is not necessary, which leads to a reduction in the manufacturing cost of the pulsimeter 2.

The measuring system according to the present invention may be used for track and field and the like. In this case, the pulsimeter 2 and the host 1 may be connected via wires. Further, according to the present invention, the object to be measured is not limited to pulse, but an oxygen saturation level or the like may be measured.

What is claimed is:

1. A pulsimeter comprising:
    a waterproof housing;
    a first panel attached to the housing;
    a pulse sensor arranged in the housing in facing relationship to the first panel for detecting pulse data;
    a display for displaying a pulse count per unit time based on the pulse data;
    a communication unit for performing data communication with an external device; and
    a controller for transmitting the pulse data to the external device via the communication unit;
    wherein, in addition to the pulse data, the pulse sensor detects identification data related to the pulse data.

2. The pulsimeter according to claim 1, wherein the pulse sensor includes a light emitting clement for irradiating a detection object, and a light receiving element for detecting light reflected by the detection object.

3. The pulsimeter according to claim 1, wherein the data communication is performed wirelessly.

4. A pulsimeter comprising:
    a waterproof housing;
    a first panel attached to the housing;
    a pulse sensor arranged in the housing in facing relationship to the first panel for detecting pulse data;
    a display for displaying a pulse count per unit time based on the pulse data;
    a communication unit for performing data communication with an external device;
    a controller for transmitting the pulse data to the external device via the communication unit;
    an identification data inputting unit provided separately from the pulse sensor for inputting identification data related to the pulse data, the controller transmitting the identification data together with the pulse data to the external device via the communication unit; and
    a second panel supported by the housing, the identification data inputting unit being arranged in the housing in facing relationship to the second panel.

5. The pulsimeter according to claim 4, wherein the housing is configured like a dome having a top, the first panel being arranged adjacent the top, the second panel being farther from the top than the first panel is.

6. The pulsimeter according to claim 1, further comprising a rechargeable power source provided in the housing, the power source being charged by an external recharging device in a non-contact manner.

* * * * *